(12) United States Patent
Craig (10) Patent No.: US 7,776,059 B2
(45) Date of Patent: Aug. 17, 2010

(54) SUTURING METHOD (76) Inventor: H Randall Craig, 3200 N. Dobson Rd. Suite F-7, Chandler, AZ (US) 85224

( * ) Notice: Subject to any disclaimer, the term of this patent is extended or adjusted under 35 U.S.C. 154(b) by 899 days.

(21) Appl. No.: 10/906,170

(22) Filed: Feb. 5, 2005

(65) Prior Publication Data

US 2005/0165414 A1 Jul. 28, 2005

Related U.S. Application Data (62) Division of application No. 10/064,235, filed on Jun. 24, 2002, now Pat. No. 6,986,776.

(60) Provisional application No. 60/302,338, filed on Jun. 28, 2001.

(51) Int. Cl.
*A61B 17/04* (2006.01)

(52) U.S. Cl. ...................................... 606/148; 606/144

(58) Field of Classification Search ................ 606/139, 606/144, 148, 218
See application file for complete search history.

(56) References Cited

U.S. PATENT DOCUMENTS

| 102,348 | A | 4/1870 | Willard |
| 2,634,674 | A | 4/1953 | Irwin |
| 3,063,360 | A | 11/1962 | Fitch et al. |
| 3,758,143 | A | 9/1973 | Godlewski |
| 4,817,514 | A | 4/1989 | Hitch et al. |
| 4,874,156 | A | 10/1989 | Goldzweig |
| 5,018,530 | A | 5/1991 | Rank |
| 5,330,503 | A | 7/1994 | Yoon |
| 5,356,424 | A | 10/1994 | Buzerak et al. |
| 5,368,595 | A | 11/1994 | Lewis |
| 5,405,376 | A | 4/1995 | Mulier |
| 5,423,836 | A | 6/1995 | Brown |
| 5,499,990 | A | 3/1996 | Schulken et al. |
| 5,545,148 | A | 8/1996 | Wurster |
| 5,562,685 | A | 10/1996 | Mollenauer |
| 5,582,616 | A | 12/1996 | Bolduc et al. |
| 5,636,984 | A | 6/1997 | Gomes |
| 5,662,683 | A | 9/1997 | Kay |
| 5,695,462 | A | 12/1997 | Sutco et al. |
| 5,709,692 | A | 1/1998 | Mollenauer et al. |
| 5,797,928 | A | 8/1998 | Kogasaka |
| 5,820,631 | A | 10/1998 | Nobles |
| 5,947,983 | A * | 9/1999 | Solar et al. .................. 606/144 |
| 6,086,601 | A | 7/2000 | Yoon |
| 6,514,263 | B1 * | 2/2003 | Stefanchik et al. .......... 606/144 |

(Continued)

*Primary Examiner*—Todd E Manahan
*Assistant Examiner*—Michael G Mendoza
(74) *Attorney, Agent, or Firm*—Oppedahl Patent Law Firm LLC (57) ABSTRACT

An apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

18 Claims, 7 Drawing Sheets

U.S. PATENT DOCUMENTS 6,626,917 B1 9/2003 Craig
6,663,633 B1 12/2003 Pierson, III 2001/0045753 A1 11/2001 Lewis

* cited by examiner

SUTURING METHOD

CROSS REFERENCE TO RELATED APPLICATIONS

This application is a divisional of U.S. application Ser. No. 10/064,235, filed Jun. 24, 2002, now U.S. Pat. No. 6,986,776, and published on Jan. 9, 2003 as U.S. 2003-0009179 A1, which claims priority from U.S. appl. No. 60/302,338 filed Jun. 28, 2001, each of which applications is incorporated herein by reference.

BACKGROUND OF INVENTION

The invention relates generally to suturing and relates more particularly to suturing in which it is desired to suture a layer of tissue without puncturing or damaging another layer of tissue.

It is well known to suture tissue, for example to close wounds and incisions in living tissue. Some historical background of suturing is found in PCT appl. no. PCT/US00/29508, filed Oct. 26, 2000, designating the United States, published as PCT publication no. WO 01/30245, published May 3, 2001 and assigned to the same assignee as the assignee of the present application, incorporated herein by reference.

One goal in suturing is to bring two tissue edges together by means of the sutures. It is also typically desired that the sutures not puncture a deeper tissue. It is also typically desired that the points at which the sutures puncture the tissue be in a particular relationship with the tissue edges. For example, it is typically desired that the points not be too close to the edges. Competing with the latter goal is the previously mentioned goal that the suture not puncture the deeper tissue.

It is also known to perform a series of sutures with the assistance of a helical suture device such as that set forth in the above-mentioned PCT application designating the United States. With such a helical suture device, it is necessary to draw some balance between large and small diameters. If the diameter is too small, the punctures may be undesirably close to the edges of the tissue being sutured. If the diameter is too large, there is the concern that the suture device may undesirably pierce the tissue below. It would thus be extremely desirable if a way could be devised in which a helical suture device could be employed to suture tissue, while minimizing the risk that the device may puncture tissue below.

SUMMARY OF INVENTION

An apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

BRIEF DESCRIPTION OF DRAWINGS

The invention is described with respect to a drawing in several figures, of which.

Where possible, like reference designations have been used amongst the figures to designate like features.

DETAILED DESCRIPTION

The present invention, a tissue shield, in combination with a helical suturing instrument, results in the placement of a continuous suture with substantially increased efficiency, and with a minimized risk of inadvertently puncturing or damaging underlying or surrounding tissue.

Figure 1:
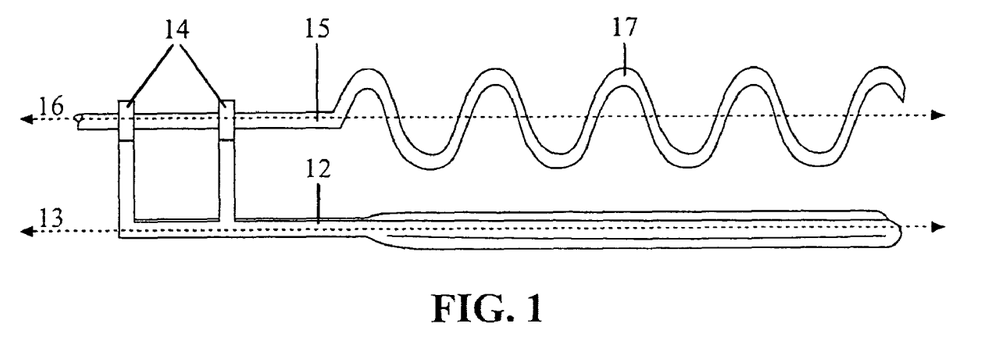
FIG. 1 is a side view of an embodiment of a tissue shield and helical suture instrument.
Figure 2:
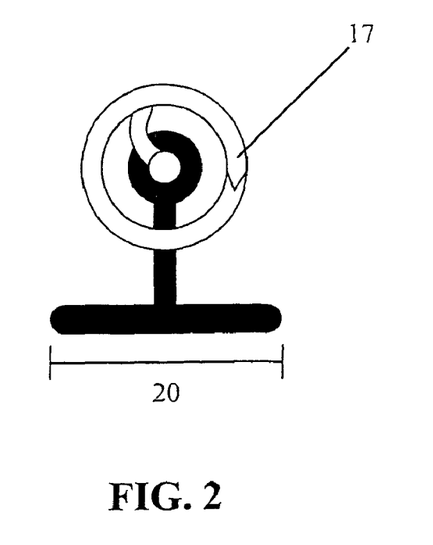
FIG. 2 is a front view of an embodiment of a spatulate member of a tissue shield and a helical suture instrument.

A first embodiment of the invention is the tissue shield itself, which comprises an apparatus having a first end 11 and a second end 12, as illustrated in FIG. 1. The first end comprises a spatulate member having a length, an embodiment of which may be greater than one inch and less than seven inches, along a first axis 13. As illustrated in FIG. 2, the spatulate member extends in a first direction and a second direction from the first axis 13, the first direction and second direction are on opposite sides of the plane. The extensions in the first and second direction from the first axis define a width 20. In an exemplary embodiment, the width defined by the extensions is less than one third of the length. It is not required, but the spatulate member may be symmetric relative to the first axis.

Figure 3:
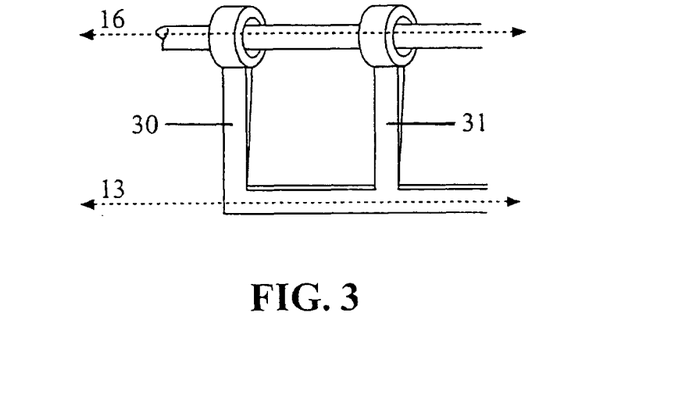
FIG. 3 is an embodiment of a guide from a tissue shield.

The second end comprises a guide 14 shaped to receive a cylindrical axle 15 for rotation on a second axis 16. A possible configuration for the guide is illustrated in FIG. 3. Here the guide comprises two members 30 and 31. Each member extends toward the second axis 16 from the first axis 13. Each of the members has a hole shaped to receive the cylindrical axle as defined below. The guide is shaped to constrain the first axis in fixed position relative and substantially parallel to the second axis, the first and second axes each lying within a plane. For this embodiment of the invention, the terms "substantially parallel" mean that the axes may be constrained to be within 15 degrees of parallel. Alternatively, the confinement angle could be 10 degrees or 5 degrees. An exemplary embodiment of this configuration is where the first and second axes are greater than one-quarter inch apart.

As shown in FIG. 1, the cylindrical axle 15 is a straight portion of a tubular member of a helical suture instrument 17 such as the one disclosed in PCT appl. no. PCT/US00/29508 published as PCT publication no. WO 01/30245. The cylindrical axle 15 is inserted into the guide for support purposes during suturing and to help prevent the tissue shield from separating from the helical suture needle. Stated differently, the guide keeps the shield positioned reliably relative to the helical suture instrument.

Figure 4:
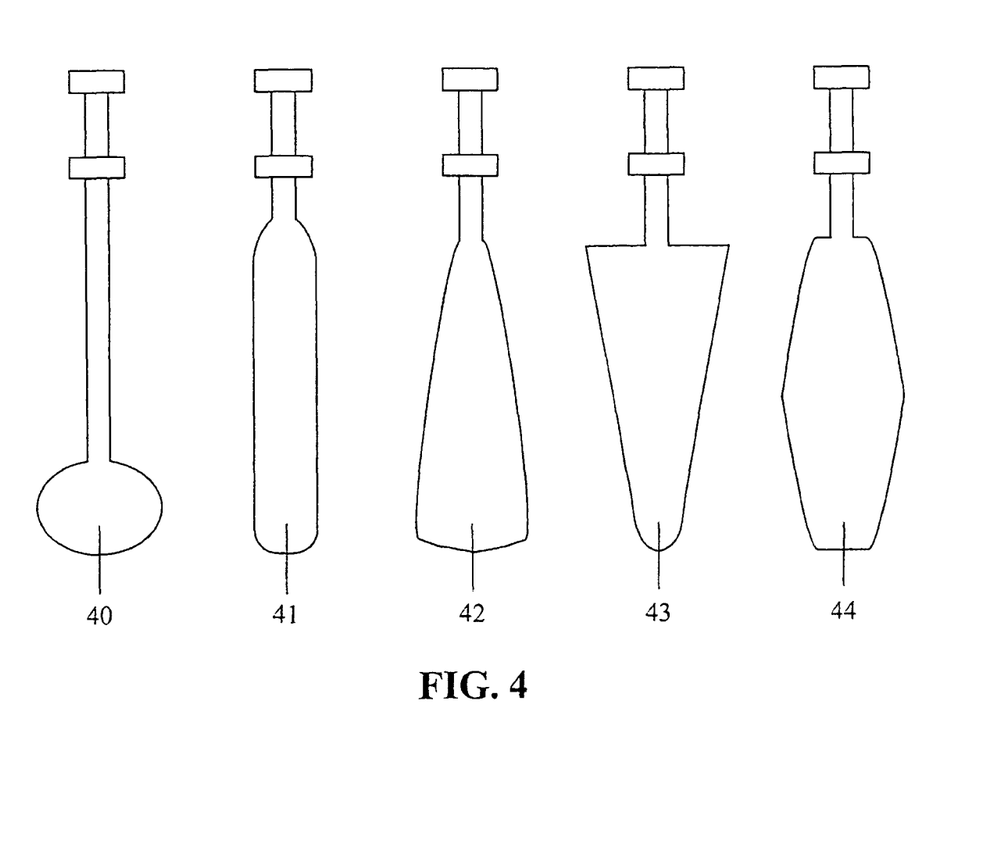
FIG. 4 is a top view of several embodiments of spatulate members.
Figure 5:
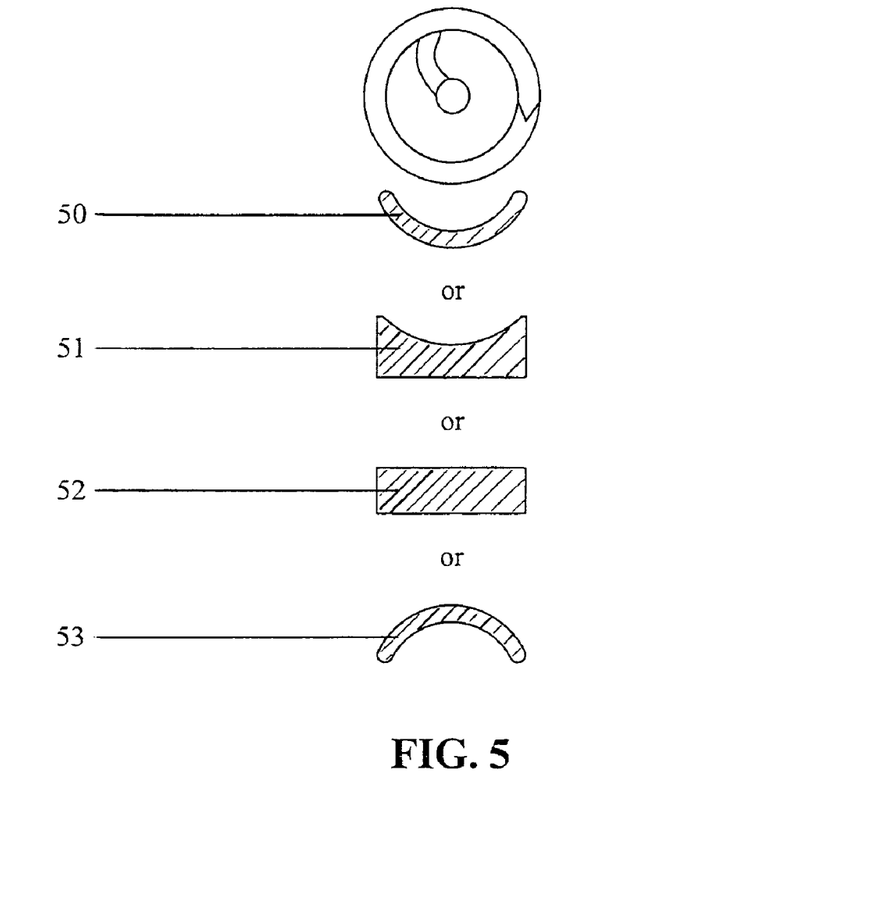
FIG. 5 is a front view of several embodiments of spatulate members.

Depending on the type and location of tissue requiring suturing, one may desire a variety of different shapes for the spatulate member of the tissue shield. Most shapes are symmetric about the first axis 13, however, this symmetry is not required. Several examples of top views of potential shapes for the spatulate member are illustrated in FIG. 4. These shapes include but are not limited to: a "T-shape" 40 which has a long skinny section with an oval shape at the end whose major axis is perpendicular to first axis 13; a "Blade" shape 41 which is a rectangle with rounded corners, a "Tapered" shape 42 which looks like a teardrop having its narrowest point at the end closest to the guide, a "Pointed" shape 43 which resembles a triangle with rounded corners having a base at the end closest to the guide, and a "Flared" shape 44 which resembles a hexagon with rounded corners. Many other shapes are possible, especially polygons with rounded corners as well as circular or elliptical shapes with continuous curves. While it is not required, it is preferred that the corners on any polygon are rounded to prevent tissue damage from sharp edges. In addition to the variations in the potential top views of the spatulate member, the member may also have differences in the surface that is located just below where a helical suture may be present. This again depends on tissue requirements or application. Several examples of potential cross sections of the tissue shields show these various shapes and are illustrated in FIG. 5. These surface shapes include but are not limited to: a surface concave about first axis 13 and a helical suturing device 50; a surface concave about first axis 13 and a helical suturing device, but having a flat base 51; a completely flat surface 52; a surface convex about first axis 13 and a helical suturing device 53; and a surface convex about first axis 13 and a helical suturing device, but having a flat base.

Figure 6:
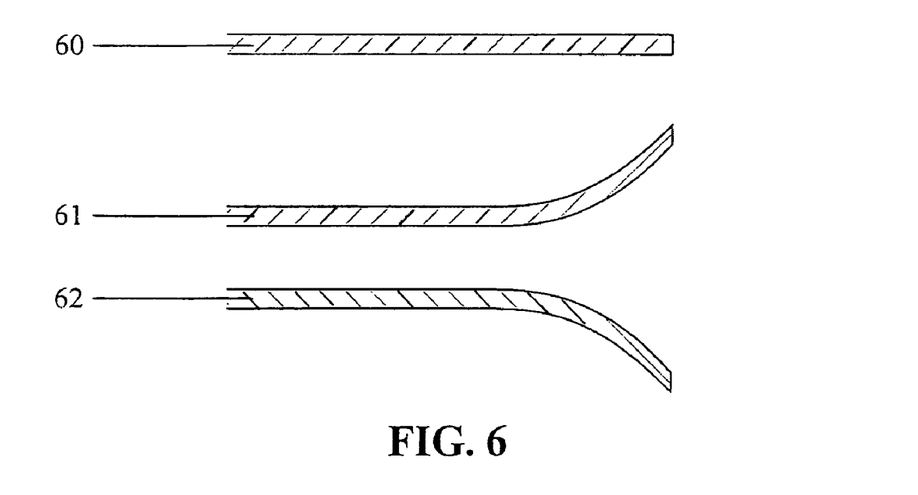
FIG. 6 is a side view of several embodiments of spatulate members.

The spatulate member of the tissue shield has a leading edge which is on the end located under a helical suture needle tip as disclosed in PCT appl. no. PCT/US00/29508 published as PCT publication no. WO 01/30245. This edge may or may not be flat 60 depending on the tissue to be sutured. It also may have, but is not limited to a leading edge that is curved upward 61 toward second axis 14 or an edge that is curved downward 62 away from the second axis 14. These general examples are illustrated in FIG. 6.

The apparatus of the tissue shield invention may be made of plastic, metal or other sufficiently hard materials. A suitable material may be non-porous to simplify sterilization. It should be stiff enough to not deform unduly when pressed against various tissue, but not so stiff that it is brittle and likely to crack or break during a procedure.

Ideally, any instrument used in a surgical or other invasive procedure is desired to be sterile. This also holds true for the tissue shield. Although it is not required during the manufacture of the invention, the shield may be sterilized be methods including but not limited to: toxic gas, heat, boiling, and gamma radiation. If the invention is sterilized during manufacture or packaging, it may be desirable to enclose the apparatus in a protective wrapper that will assist in the preservation of sterility. Whether or not the tissue shield is to be sterilized during manufacture, it is desirable that the surface of the tissue protector be extremely smooth to help aid in any sterilization process.

A second embodiment of the invention is a helical suture instrument 10 (FIG. 1) as disclosed in PCT appl. no. PCT/US00/29508 published as PCT publication no. WO 01/30245 and tissue protecting apparatus as described above. The helical suture instrument has a cylindrical axle which defines the second axis, and a helical portion having a helical outer diameter. The helical suture instrument also has second axial length along the second axis. More descriptive detail is provided in the above referenced PCT application.

Figure 7:
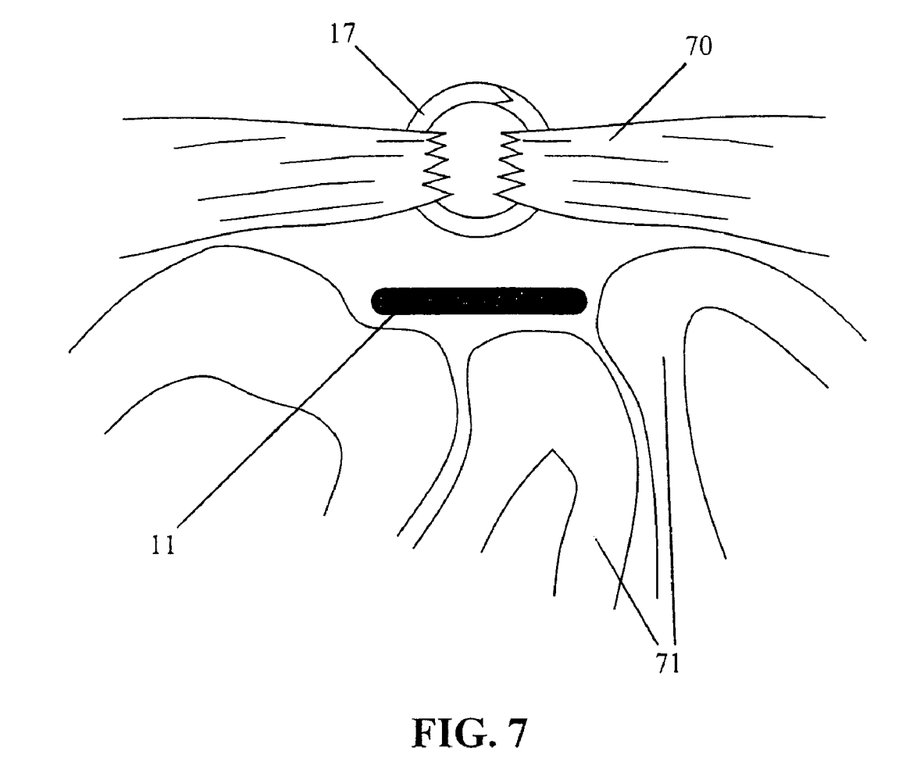
FIG. 7 is an illustration of the tissue shield and helical suturing instrument may be placed during use.
Figure 8:
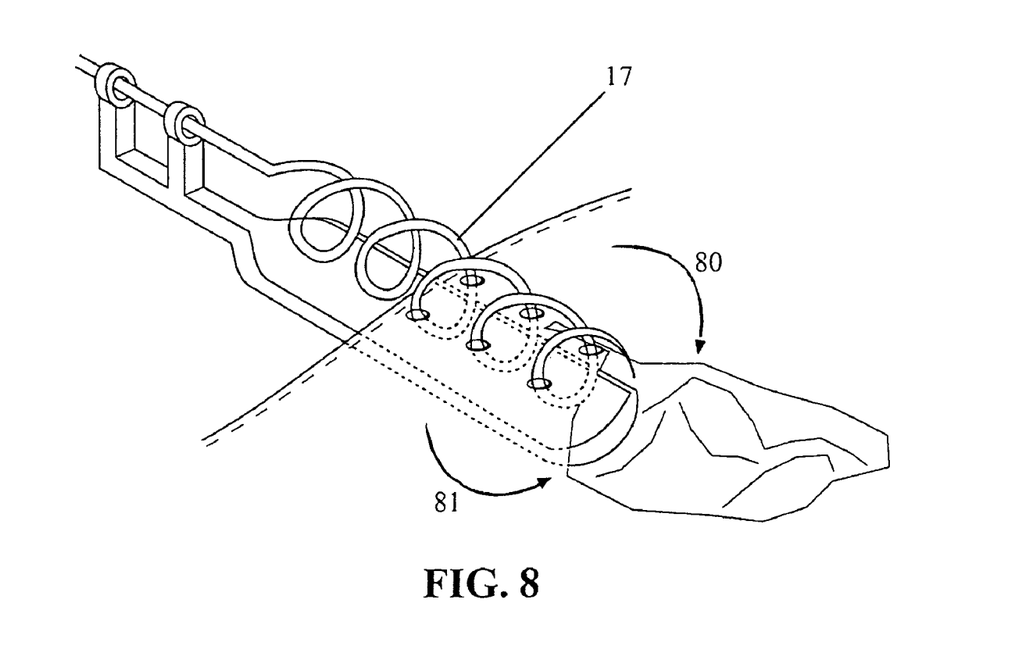
FIG. 8 is an illustration of a helical suturing instrument in use.

A suturing method performed with the apparatus of the helical suture needle and tissue shield described above comprises the following steps. First the spatulate member is placed between the first and second tissues. As may be seen in FIG. 7, the spatulate member presses against the second tissue, separating it from the first tissue. The first tissue 70 is the tissue desired to be sutured, and the second tissue 71 is the tissue requiring protection from becoming damaged during the procedure. See FIG. 7 for an illustration of placement of the system. The second step is to rotate the helical suture instrument in a first direction 80 to pierce alternately the first and second edges of the first tissue. This direction may be clockwise or counterclockwise depending on the position of the sharp end of the helical suture needle and the direction of its turns. See FIG. 8 for an illustration of this process. The third step is to rotate the helical suture instrument in a second direction 81, which is the opposite of the first, to withdraw the helical suture instrument from the first tissue. The final step is to withdraw the spatulate member from between the first and second tissues as the helical suture instrument is rotated in the second direction.

As was described in detail by PCT Publication no WO 01/30245, which was incorporated herein by reference, embodiments of the methods for attaching suturing material to the helical suture instrument, depositing the material along a path, increasing the tension on the suture, and tying a knot in the suture are also described below.

The suture material may either be "pushed" or "pulled" by the helical suturing instrument.

Figure 9:
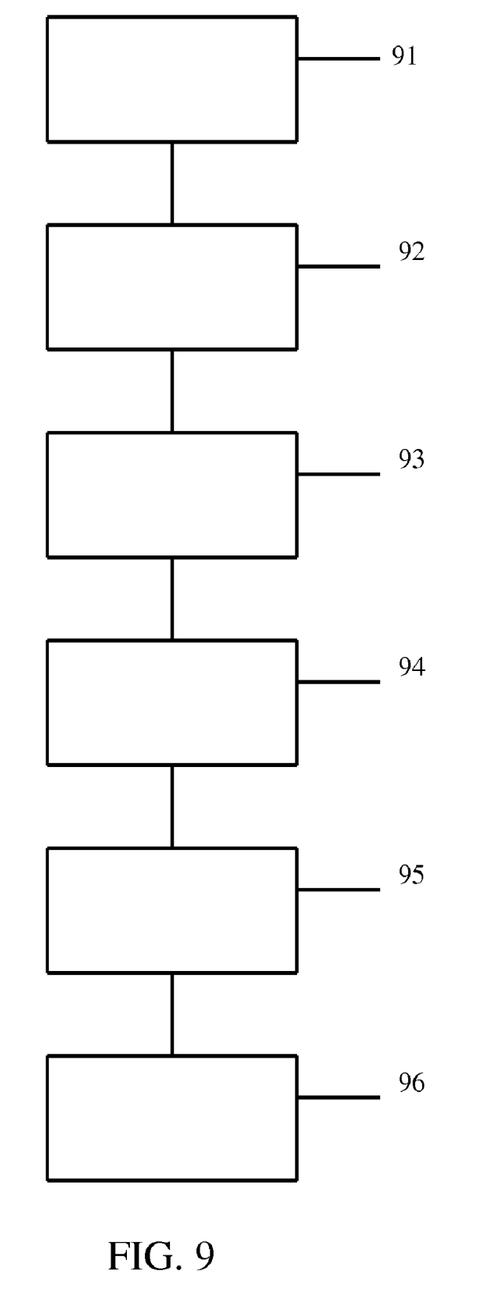
FIG. 9 is a flow diagram of the steps for "pulling" suturing material through an incision.

If the suture material is "pulled", one embodiment of the invention is described by the steps illustrated in FIG. 9. The helical suturing instrument is advanced through the incision tissue by rotation (91). The suture material is temporarily attached to the tip of the helical suturing instrument (92). The helical suturing instrument is withdrawn out of the tissue by counter-rotation while carrying the suture material through the helical track (93). After the helical suturing instrument is withdrawn by counter-rotation, the suture material is left behind in the helical needle track (94). The suture material is pulled taut (95). Finally the suture material is tied to close the incision (96).

Figure 10:
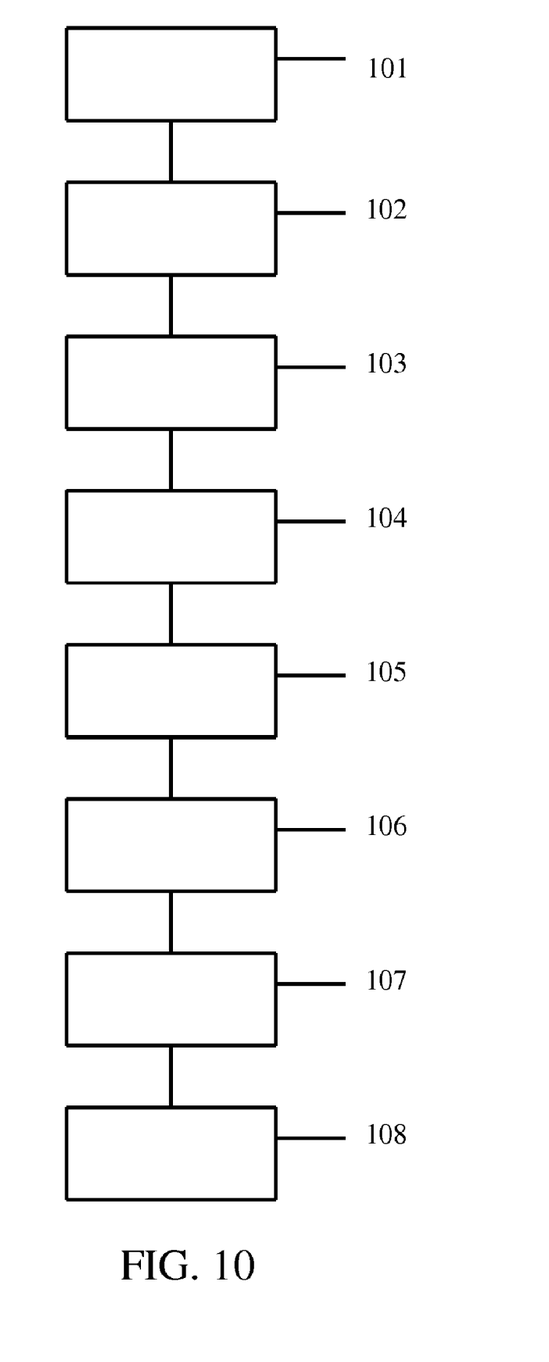
FIG. 10 is a flow diagram of the steps for "pushing" suturing material through an incision.

If the suture material is "pushed", one embodiment of the invention is described by the steps illustrated in FIG. 10. The suture material is temporarily attached to the tip of the helical suturing instrument (101). The helical suturing instrument is advanced through the incision tissue by rotation (102), repeatedly entering one side and exiting the other side of the incision, dragging the suturing material along. Once the end of the incision has been reached, further rotation of the needle is stopped (103) with the needle tip exposed in the upper portion of the incision. With the needle tip exposed, the end of the suture is detached from the needle (104) and held in place (105). The helical suturing instrument is then counter-rotated through the tissue (106) until it has been withdrawn, leaving the suture material in place along the needle track. The suturing material is pulled taut (107). Finally the suture material is tied to close the incision (108).

Figure 11:
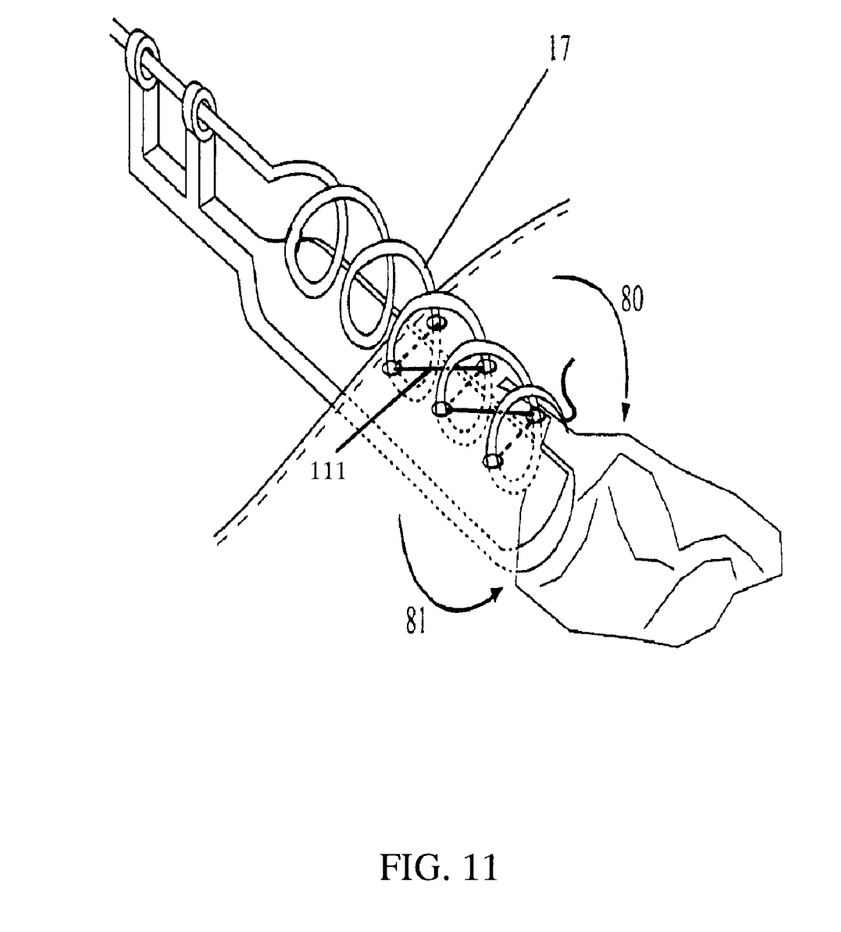
FIG. 11 is an illustration of suturing material deposited with the "pushing" method.

An exemplary embodiment of the suturing material (111) left in the track by the helical suturing instrument using the pushing method is shown in FIG. 11.

As described in detail by PCT Publication WO 01/30245, a means for attaching a suture near the tip of the helical suturing instrument may be a catch, hook, or notch in the outer surface of the helical suturing instrument near the tip, a hole through the helical suturing instrument near the tip, or any other means of removably attaching a suture to the helical suturing instrument.

What is claimed is:

1. A suturing method performed with a system comprising a helical suture instrument and apparatus, the apparatus having a first end and a second end, the first end comprising a spatulate member, the method performed with respect to a first tissue that has been incised, yielding first and second edges to be sutured together, and a second tissue, the method comprising the steps of:
   placing the spatulate member between the first and second tissues, thereby separating the second tissue from the first tissue;
   rotating the helical suture instrument in a first direction to pierce alternately the first and second edges of the first tissue, said spatulate member further characterized in that it shields said second tissue from being pierced by the helical suture instrument while said first tissue is being pierced; and
   withdrawing the spatulate member from between the first and second tissues.

2. The method of claim 1 further comprising the step of rotating the helical suture instrument in a second direction to withdraw the helical suture instrument from the first tissue.

3. The method of claim 2 wherein the spatulate member is withdrawn from the first and second tissues as the helical suture instrument is rotated in the second direction.

4. The method of claim 2 wherein the spatulate member is withdrawn from the first and second tissues prior to the helical suture instrument being rotated in the second direction.

5. The method of claim 2 wherein the spatulate member is withdrawn from the first and second tissues after the helical suture instrument is rotated in the second direction.

6. The method of claim 2 further comprising the step of attaching a suture to a location on the helical suture instrument.

7. The method of claim 6 wherein the step of attaching a suture to a location on the helical suture instrument occurs prior to rotating the helical suture instrument in a first direction.

8. The method of claim 6 wherein the step of attaching a suture to a location on the helical suture instrument occurs after rotating the helical suture instrument in a first direction and prior to rotating the helical suture instrument in a second direction to withdraw the helical suture instrument from the first tissue.

9. A method performed with a system comprising a helical suture instrument and apparatus, the apparatus having a first end and a second end, the first end comprising a spatulate member, the method performed with respect to a first tissue that has been incised, yielding first and second edges to be sutured together, and a second tissue, the helical suture instrument being threaded through the first and second edges of the first tissue, the apparatus being positionable between the first and second tissues, the method comprising the steps of:
   inserting the spatulate member between the first and second tissues, thereby separating the second tissue from the first tissue;
   rotating the helical suture instrument in a direction to withdraw the helical suture instrument from the first and second edges of the first tissue, said spatulate member further characterized in that it shields said second tissue from being pierced by the helical suture instrument; and
   withdrawing the spatulate member from between the first and second tissues.

10. The method of claim 9 wherein the spatulate member is withdrawn from between the first and second tissues as the helical suture instrument is rotated to withdraw the helical suture instrument from the first and second edges of the first tissue.

11. The method of claim 9 wherein the spatulate member is withdrawn from between the first and second tissues after the helical suture instrument is rotated to withdraw the helical suture instrument from the first and second edges of the first tissue.

12. The method of claim 9 wherein the spatulate member is withdrawn from between the first and second tissues before the helical suture instrument is rotated to withdraw the helical suture instrument from the first and second edges of the first tissue.

13. A suturing method performed with a system comprising a helical suture instrument and apparatus, the apparatus having a first end and a second end, the first end comprising a spatulate member, the method performed with respect to a first tissue that has been incised, yielding first and second edges to be sutured together, and a second tissue, the method comprising the steps of:
   placing the spatulate member between the first and second tissues, thereby separating the second tissue from the first tissue;
   creating a path for a suture by rotating the helical suture instrument in a first direction to pierce alternately the first and second edges of the first tissue, said spatulate member further characterized in that it shields said second tissue from being pierced by the helical suture instrument while said first tissue is being pierced;
   depositing the suture along the path; and
   withdrawing the spatulate member from between the first and second tissues.

14. The method of claim 13 further comprising the step of rotating the helical suture instrument in a second direction to withdraw the helical suture instrument from the first tissue.

15. The method of claim 14 wherein the suture is deposited along the path as the helical suture instrument is rotated in a first direction.

16. The method of claim 14 wherein the suture is deposited along the path as the helical suture instrument is rotated in a second direction.

17. The method of claim 14 further comprising the step of increasing the tension on the suture after it has been deposited along the path.

18. The method of claim 14 further comprising the step of tying at least one knot in the suture.

* * * * *